US011389435B2

(12) United States Patent
Deftereos et al.

(10) Patent No.: US 11,389,435 B2
(45) Date of Patent: Jul. 19, 2022

(54) COMPOSITIONS AND METHODS FOR TREATING EPILEPSY

(71) Applicant: BIOVISTA, INC., Charlottesville, VA (US)

(72) Inventors: Spyros Deftereos, Athens (GR); Andreas Persidis, Athens (GR)

(73) Assignee: BIOVISTA, INC., Charlottesville, VA (US)

( * ) Notice: Subject to any disclaimer, the term of this patent is extended or adjusted under 35 U.S.C. 154(b) by 0 days.

(21) Appl. No.: 16/784,362

(22) Filed: Feb. 7, 2020

(65) Prior Publication Data
US 2020/0345710 A1 Nov. 5, 2020

Related U.S. Application Data

(63) Continuation of application No. 14/251,819, filed on Apr. 14, 2014, now abandoned, which is a continuation of application No. 13/063,873, filed as application No. PCT/US2009/056988 on Sep. 15, 2009, now abandoned.

(60) Provisional application No. 61/183,209, filed on Jun. 2, 2009, provisional application No. 61/096,940, filed on Sep. 15, 2008.

(51) Int. Cl.
A61K 31/444 (2006.01)
A61P 25/08 (2006.01)
A61K 31/437 (2006.01)

(52) U.S. Cl.
CPC .......... A61K 31/444 (2013.01); A61K 31/437 (2013.01); A61P 25/08 (2018.01)

(58) Field of Classification Search
CPC ...... A61K 31/444; A61K 31/437; A61P 25/08
See application file for complete search history.

(56) References Cited

U.S. PATENT DOCUMENTS

| 3,536,809 | A | 10/1970 | Applezweig |
| 3,539,573 | A | 11/1970 | Schmutz |
| 3,598,123 | A | 8/1971 | Zaffaroni |
| 3,630,200 | A | 12/1971 | Higuchi |
| 3,847,770 | A | 11/1974 | Radlowe |
| 3,916,899 | A | 11/1975 | Theeuwes |
| 3,959,470 | A | 5/1976 | Mashkovsky |
| 4,008,719 | A | 2/1977 | Theeuwes |
| 4,687,610 | A | 8/1987 | Vassilatos |
| 4,769,027 | A | 9/1988 | Baker |
| 4,879,288 | A | 11/1989 | Warawa |
| 5,059,595 | A | 10/1991 | Le Grazie |
| 5,073,543 | A | 12/1991 | Marshall |
| 5,120,548 | A | 6/1992 | McClelland |
| 5,354,566 | A | 10/1994 | Addesso |
| 5,591,767 | A | 1/1997 | Mohr |
| 5,627,165 | A | 5/1997 | Glazier |
| 5,639,476 | A | 6/1997 | Oshlack |
| 5,674,533 | A | 10/1997 | Santus |
| 5,733,566 | A | 3/1998 | Lewis |
| 5,824,676 | A | 10/1998 | Tehim |
| 7,041,661 | B2 | 5/2006 | Zhu |
| 7,071,206 | B2 | 7/2006 | Zefirov |
| 7,214,673 | B2 | 5/2007 | Aicher |
| 7,550,143 | B2 | 6/2009 | Chang |
| 7,790,712 | B2 | 9/2010 | Cogan |
| 2002/0016301 | A1 | 2/2002 | Godek |
| 2003/0171270 | A1 | 9/2003 | Civelli |
| 2004/0102525 | A1 | 5/2004 | Kozachuk |
| 2004/0228923 | A1 | 11/2004 | Bartus |
| 2005/0014729 | A1 | 1/2005 | Pulaski |
| 2005/0065219 | A1 | 3/2005 | Lipton |
| 2005/0171032 | A1 | 8/2005 | Solomon |
| 2005/0245460 | A1 | 11/2005 | Meyerson |
| 2006/0154968 | A1 | 7/2006 | Ehring |
| 2007/0027178 | A1 | 2/2007 | Lee |
| 2007/0149452 | A1 | 6/2007 | Marshall |
| 2007/0150024 | A1 | 6/2007 | Leyde |
| 2007/0270429 | A1 | 11/2007 | Shibayama |
| 2008/0108574 | A1 | 5/2008 | Barlow |
| 2008/0176828 | A1 | 7/2008 | Williams |
| 2009/0143279 | A1 | 6/2009 | Mootha |
| 2010/0178277 | A1 | 7/2010 | Hung |
| 2011/0111014 | A1 | 5/2011 | Langston |
| 2011/0268699 | A1 | 11/2011 | Deftereos |

FOREIGN PATENT DOCUMENTS

| JP | 9216882 | 8/1997 |
| RU | 2281085 | 10/2006 |
| WO | 2006048242 | 5/2006 |
| WO | 2008036410 | 3/2008 |
| WO | 2008051599 | 5/2008 |
| WO | 2008133884 | 11/2008 |
| WO | 2008147551 | 12/2008 |
| WO | 2009095265 | 8/2009 |

(Continued)

OTHER PUBLICATIONS

Acar, G., et al. "Nitric oxide as an activity marker in multiple sclerosis." Journal of neurology 250.5 (2003): 588-592.
Boland, André, et al. "Pirlindole and dehydropirlindole protect rat cultured neuronal cells against oxidative stress☐ induced cell death through a mechanism unrelated to MAO☐ A inhibition." British journal of pharmacology 135.3 (2002): 713-720.
Gonsette, R. E. "Neurodegeneration in multiple sclerosis: the role of oxidative stress and excitotoxicity." Journal of the neurological sciences 274.1 (2008): 48-53.
Supplementary European Search Report for EP 09 83 2613, dated Mar. 13, 2012, 4 pages.
International Preliminary Report on Patentability for PCT/US2009/067673, dated Jun. 14, 2011, 7 pages.

(Continued)

Primary Examiner — Kara R McMillian
(74) Attorney, Agent, or Firm — Brannon Sowers & Cracraft PC

(57) ABSTRACT

Compositions and methods for treating epilepsy and epileptic syndromes are described herein. The compositions and methods include therapeutically effective amounts of one or more dimebolins, or pharmaceutically acceptable salts thereof.

20 Claims, No Drawings

(56) References Cited

FOREIGN PATENT DOCUMENTS

WO  2009135091  11/2009
WO  2010045265  4/2010

OTHER PUBLICATIONS

Farrell, Rachel, Dominic Heaney, and Gavin Giovannoni. "Emerging therapies in multiple sclerosis." Expert opinion on emerging drugs 10.4 (2005): 797-816.
Anonymous, "Biovista Announces Positive Efficacy Results in a Pre-Clinical Trial of BVA-201 for Multiple Sclerosis," Sep. 9, 2009.
Anonymous, "Biovista Announces Positive Efficacy Results in a Pre-Clinical Trial of BVA-201 for Multiple Sclerosis," Apr. 2, 2009.
PCT International Search Report/Written Opinion for PCT/US2009/067673, completed Jan. 19, 2010.
Vincent, Andrea M., et al. "Identification of candidate drugs for the treatment of ALS." Amyotrophic Lateral Sclerosis 6.1 (2005): 29-36.
Anonymous, "Biovista Announces Positive Efficacy Results in a Pre-Clinical Trial of BVA-201 for Epilepsy," Jun. 23, 2009.
PCT International Search Report/Written Opinion for PCT/US2009/056988, completed Oct. 15, 2009.
Supplementary EP Search Report for EP 09813797, dated Mar. 16, 2012, 2 pages.
Deckers, Charles LP, et al. "Selection of antiepileptic drug polytherapy based on mechanisms of action: the evidence reviewed." Epilepsia 41.11 (2000): 1364-1374.
Muraki, Takamura, Yasushi Yamazoe, and Ryuichi Kato. "Inhibition of benzodiazepine and GABA receptor binding by amino-γ-carbolines and other amino acid pyrolysate mutagens." European journal of pharmacology 98.1 (1984): 35-44.
PCT International Search Report/Written Opinion for PCT/US2013/027722, completed May 8, 2013.
Rüegg, Curzio, Jelena Zaric, and Roger Stupp. "Non steroidal anti‐inflammatory drugs and COX‐2 inhibitors as anti‐cancer therapeutics: hypes, hopes and reality." Annals of medicine 35.7 (2003): 476-487.
Roberts, Joan E., Allan F Wiechmann, and Dan‐Ning Hu. "Melatonin receptors in human uveal melanocytes and melanoma cells." Journal of pineal research 28.3 (2000): 165-171.
Sarkisian, Matthew R. "Overview of the current animal models for human seizure and epileptic disorders." Epilepsy & Behavior 2.3 (2001): 201-216.
Bachurin, S., et al. "Antihistamine agent Dimebon as a novel neuroprotector and a cognition enhancer." Annals of the New York Academy of Sciences 939.1 (2001): 425-435.
Yen, W., Williamson, J., Bertram, E. H., & Kapur, J. (2004). A comparison of three NMDA receptor antagonists in the treatment of prolonged status epilepticus. Epilepsy research, 59(1), 43-50.
Grigor'ev, V. V., Dranyi, O. A., & Bachurin, S. O. (2003). Comparative study of action mechanisms of dimebon and memantine on AMPA-and NMDA-subtypes glutamate receptors in rat cerebral neurons. Bulletin of experimental biology and medicine, 136(5), 474-477.
Saxena, V. C., Bapat, S. K., & Dhawan, B. N. (1969). An experimental evaluation of the anticonvulsant activity of some antihistaminic drugs. The Japanese Journal of Pharmacology, 19(4), 477-484.
Mathis, C., and A. Lingerer. "Comparative analysis of seizures induced by intracerebroventricular administration of NMDA, kainate and quisqualate in mice." Experimental brain research 88.2 (1992): 277-282.
Lason, W., Simpson, J. N., & McGinty, J. F. (1988). Effects of d-(−)-aminophosphonovalerate on behavioral and histological changes induced by systemic kainic acid. Neuroscience letters, 87(1-2), 23-28.
Stafstrom, C. E., Tandon, P., Hori, A., Liu, Z., Mikati, M. A., & Holmes, G. L. (1997). Acute effects of MK801 on kainic acid-induced seizures in neonatal rats. Epilepsy research, 26(2), 335-344.

COMPOSITIONS AND METHODS FOR TREATING EPILEPSY

CROSS-REFERENCE TO RELATED APPLICATIONS

This application is a continuation of U.S. patent application Ser. No. 14/251,819, filed Apr. 14, 2014, which is a continuation of U.S. patent application Ser. No. 13/063,873, filed Mar. 14, 2011, which is a U.S. national application under 37 C.F.R. § 371(b) of International Application Serial No. PCT/US2009/056988 filed Sep. 15, 2009, which claims priority under 35 U.S.C. § 119(e) to U.S. Provisional Application Ser. No. 61/096,940 filed on Sep. 15, 2008, and U.S. Provisional Patent Application Ser. No. 61/183,209 filed on Jun. 2, 2009, the entire disclosures of each of which are incorporated herein by reference.

TECHNICAL FIELD

The present invention relates to methods for treating epilepsy and epileptic syndromes. In particular, the invention relates to methods for treating epilepsy and epileptic syndromes by administering a therapeutically effective amount of one or more dimebolins.

BACKGROUND AND SUMMARY OF THE INVENTION

Epilepsy is a common chronic neurological disorder that is characterized by recurrent unprovoked seizures. These seizures may be transient signs and/or symptoms due to abnormal, excessive or synchronous neuronal activity in the brain (Fisher et al., Epilepsia 46(4):470-2 (2005)). The foregoing publication, and each additional publication cited herein is incorporated herein by reference.

In most studies, the overall incidence of epilepsy, with the exception of febrile convulsions and single seizures, in developed societies has been found to be around 50 cases per 100,000 persons per year, but in some years as many as 70 per 100,000 have been reported. Surprising, the figures for developing countries are generally higher, and range from 100 to 190 per 100,000 each year. Though not confirmed, it has been suggested that the higher occurrence may be due to social deprivation. For example, recent data suggest that people from socioeconomically deprived backgrounds in developed countries are more likely to develop epilepsy.

The lifetime prevalence of seizures, namely, the risk of having a nonfebrile epileptic seizure at some point in an average lifetime, is between 2 and 5%. In recent community based studies, it has been shown that for most patients epilepsy is relatively short-lived; over two thirds enter long-term remission and once remission has occurred, subsequent relapses are uncommon. In fact, the course of the condition in its early years is an important predictor of prognosis; the longer epilepsy remains active the poorer the long-term prognosis. The cumulative incidence of febrile seizures, namely the risk of having a febrile seizure before the age of five, is about 5%, and febrile seizures account for a substantial proportion of seizures in children under five.

Epileptic seizures typically involve excessive firing and synchronization of neurons. This condition interrupts the normal working of the parts of the brain involved, and in some cases leads to impaired consciousness. Localization related epilepsies arise in the neocortex and limbic structures including the hippocampus and amygdala. Work on a range of experimental models produced detailed theories on the generation of brief (ca. 100-500 ms) epileptic events analogous to the interictal spikes often found in the EEGs of humans with partial seizures. However, theories on full-blown seizures are less well developed at present. Experimental interictal discharges are reportedly characterized by abrupt paroxysmal depolarization shifts that occur synchronously in the majority of neurons in the local area. Such large depolarizations of 20-40 mV make the neurons fire rapid bursts of action potentials. In general, paroxysmal depolarization shifts have properties of a giant excitatory postsynaptic potential (EPSP), and depends on glutamate, the main excitatory synaptic transmitter in the brain. It has been reported that it is the sum of simultaneous excitation from many other neurons within the same population. In addition, contributions from voltage sensitive calcium channels, which can produce slow action potentials, which may drive neurons above the threshold for the fast action potentials, due to voltage sensitive sodium channels have been implicated.

Combined experimental and theoretical work on many experimental models show that several features are necessary for this kind of epileptic discharge. Excitatory (usually pyramidal) neurons must be connected into a synaptic network. The probability of such connections can be as little as 1-2% of randomly chosen pairs of pyramidal cells in the hippocampus. The synapses need to be strong enough, because of the properties of the synapse and/or because of the firing pattern of the presynaptic neuron. For example, burst firing reportedly indicates that synaptic potentials can be additive. Therefore, neurons need to have a good chance of driving their postsynaptic targets above threshold, and the population of neurons must also be large enough, and constitute the minimum aggregate. This minimum aggregate allows neurons to connect with almost all the others in the population within a few synapses with the result that activity in a small subset of neurons can spread through the population very rapidly under the right conditions. In experimental models the minimum epileptic aggregate can be as low as 1000-2000 neurons, but probably is larger in human epileptic foci. Acute experimental epilepsies, using convulsant treatments on normal brain tissue, have been suggested to model symptomatic seizures.

Such acute experimental epilepsies may modify synaptic networks by several routes or combinations of routes. For example, synaptic networks may be modified by blocking inhibitory synapses (using GABA as their transmitter) that normally control the excitation of the excitatory synaptic network. This blocking is typical of many convulsants used experimentally, such as has been reported with pentylenetetrazol (PTZ) and bicuculline, and can occur clinically, such as has been reported with penicillin and quinolones, under certain conditions. Alternatively, or in combination, synaptic networks may be modified paradoxically. For example. excessive activation of GABA-A mediated synapses can switch them from inhibitory to excitatory and thus promote epileptic activity. This effect may be due to a collapse of the gradient of chloride ions across the membrane, leaving bicarbonate ions as the main charge carrier at these synapses. Synaptic networks may be modified by strengthening excitatory synapses, for instance with abnormally low levels of extracellular magnesium ions unblocking the NMDA subtype of glutamate receptor, or by increasing neuronal excitability.

Other factors also contribute to epileptic discharges. Chronic experimental models, and where it is possible to make the appropriate measurements in human localization related epilepsies, reveal multiple changes which occur in various combinations in specific examples. For example, increased synaptic connectivity is a common feature, and perhaps most reported in mossy fibre sprouting, may promote the chain reaction recruitment of excitatory, glutamatergic neurons outlined above.

In addition, intrinsic properties are also involved. Voltage gated ion channels change in many epilepsies, which may be profound in the small minority of epilepsies that are genetic channelopathies. In some forms of epilepsy, potassium channels are weakened, while in others, sodium channels may become more persistent. In those cases the mutation is presumably a primary factor in epileptogenesis. Changes in voltage gated ion channels also can be found in much more common epilepsies that do not have an obvious genetic basis, for instance temporal lobe epilepsy where sodium channel inactivation is delayed (often in parallel with a loss of sensitivity to carbamazepine).

Synaptic receptors can also be different in epileptic tissue. Again the inherited channelopathies exhibit examples of altered GABAergic receptors (tending to depress inhibitory potentials), and of changes in nicotinic receptors. Other studies of more common idiopathic epilepsies reveal alterations in expression of specific receptor subunits.

While interictal discharges have been reported as commonly associated with localization related epilepsy, it has been suggested that they probably are generated by different, or at least non-identical, circuits from seizures. Moreover, their role in seizure generation is not well understood, nor accepted. Results from some experimental models suggest that interictal discharges may help prevent prolonged seizures getting started, by mechanisms yet to be determined. Other studies suggest that interictal discharges may come in more than one variety, some of which tend to precipitate seizures. Studies continue as to which factors determine whether an epileptic discharge develops into a full-blown seizure. For example, it has been reported that during the first few seconds of a seizure discharge, concentrations of extracellular potassium ions increase from the normal of about 30-40 mM to a high level of greater than about 1000 mM, which in turn excites neurons, with a relatively slow time course. However, extracellular potassium appears to accumulate too slowly to be the trigger for seizures, so the mechanisms that sustain synchronous activity for the first few seconds may be more important. The dynamics of the handling of extracellular potassium and other neuroactive substances by neurons and glia during seizures is also an active area of research.

It has been discovered that dimebolins, including dimebon itself (also known as dimebolin hydrochloride) and analogs and derivatives thereof, as well as pharmaceutically acceptable salts of the foregoing, are useful in treating patients suffering from or in need of relief from epilepsy and/or epileptic syndromes.

In one illustrative embodiment of the invention, methods for treating epilepsy are described. In another illustrative embodiment of the invention, methods for treating epileptic syndromes are described. In each of the foregoing, the methods include the step of administering a therapeutically effective amount of one or more dimebolins, and/or pharmaceutically acceptable salts thereof, to a patient suffering from, or in need of relief from epilepsy and/or epileptic syndrome. In another embodiment, methods are described herein that include the step of administering a therapeutically effective amount of one or more dimebolins, and/or pharmaceutically acceptable salts thereof, and administering a therapeutically effective amount of one or more NMDA receptor antagonists to a patient suffering from, or in need of relief from epilepsy and/or epileptic syndrome. In another embodiment, methods are described herein that include the step of administering a therapeutically effective amount of one or more dimebolins, and/or pharmaceutically acceptable salts thereof, and administering a therapeutically effective amount of one or more AMPA receptor antagonists to a patient suffering from, or in need of relief from epilepsy and/or epileptic syndrome. In another embodiment, methods are described herein that include the step of administering a therapeutically effective amount of one or more dimebolins, and/or pharmaceutically acceptable salts thereof, and administering a therapeutically effective amount of one or more additional anti-epileptic drugs to a patient suffering from, or in need of relief from epilepsy and/or epileptic syndrome. In another embodiment, methods are described herein that include the step of administering a therapeutically effective amount of one or more dimebolins, and/or pharmaceutically acceptable salts thereof, administering a therapeutically effective amount of one or more NMDA receptor antagonists, and administering a therapeutically effective amount of one or more additional anti-epileptic drugs to a patient suffering from, or in need of relief from epilepsy and/or epileptic syndrome.

In another illustrative embodiment of the invention, uses of dimebolins and pharmaceutically acceptable salts thereof in the manufacture of medicaments for treating epilepsy and epileptic syndromes are described. In each of the foregoing, the medicaments include a therapeutically effective amount of one or more dimebolins, and/or pharmaceutically acceptable salts thereof. In another embodiment, the medicaments include a therapeutically effective amount of one or more dimebolins, and/or pharmaceutically acceptable salts thereof, and a therapeutically effective amount of one or more NMDA receptor antagonists. In another embodiment, the medicaments include a therapeutically effective amount of one or more dimebolins, and/or pharmaceutically acceptable salts thereof, and a therapeutically effective amount of one or more AMPA receptor antagonists. In another embodiment, the medicaments include a therapeutically effective amount of one or more dimebolins, and/or pharmaceutically acceptable salts thereof, and a therapeutically effective amount of one or more additional anti-epileptic drugs. In another embodiment, the medicaments include a therapeutically effective amount of one or more dimebolins, and/or pharmaceutically acceptable salts thereof, a therapeutically effective amount of one or more NMDA receptor antagonists, and a therapeutically effective amount of one or more additional anti-epileptic drugs.

In another embodiment, the methods described herein include the co-administration of a therapeutically effective amount of one or more statins. It is to be understood that the one or more statins may be co-administered in each of the foregoing embodiments, and other embodiments described herein, including but not limited to co-administration with one or more dimebolins, co-administration with one or more dimebolins and NMDA antagonists, co-administration with one or more dimebolins, NMDA antagonists, and other anti-epileptic drugs, and the like.

In another illustrative embodiment, pharmaceutical compositions are described herein. Illustrative pharmaceutical compositions include various dosage forms of dimebolins and/or pharmaceutically acceptable salts thereof in combination with one or more pharmaceutically acceptable carriers, excipients, and/or diluents therefor. Other illustrative pharmaceutical compositions include various dosage forms of (a) one or more dimebolins and one or more NMDA antagonists, including mixtures thereof (b) one or more dimebolins and one or more and one or more other antiepileptic drugs, including mixtures thereof; (c) one or more dimebolins, one or more and one or more other anti-epileptic drugs, and one or more NMDA antagonists, including mixtures thereof, and (d) any of the foregoing also including one or more statins, including mixtures thereof. In each of the foregoing, it is to be understood that pharmaceutically acceptable salts of any of the dimebolins, NMDA antagonists, other anti-epileptic drugs, and/or statins, and the like are included. It is also to be understood that the dosage forms described herein that include mixtures, also include sandwich-type formulations where two or more separate drug dosage forms are adhered one to the other for simultaneous co-administration.

In another illustrative embodiment, kits and packages are described herein. Illustrative kits and packages include preparations where the compounds are adapted for co-administered, such as being placed in a format following the dosing protocols described herein. For example, an illustrative package may include a grid pattern, wherein each section includes a dual bubble pack for the dimebolin dosage and illustratively the NMDA antagonist dosage. It is appreciated that other configurations that include the anti-epileptic drug, or both the NMDA antagonist and anti-epileptic drug, or alternatively a statin are also described herein.

DETAILED DESCRIPTION

Dimebolins are known antihistamine drugs. In particular, dimebolin hydrochloride has been used clinically for many years (Matveeva, Farmakologiia i Toksikologiia, 46(4):27-29 (July-August 1983)), and has recently shown potential in the treatment of Alzheimer's disease (Doody et al., Lancet 372:207-215 (2008)). However, the beneficial use of dimebolins in treating epilepsy has heretofore been unknown. Without being bound by theory, it is believed herein that dimebolins may exert their actions in treating epilepsy and epileptic syndromes via multiple mechanisms. Illustratively, it has been discovered herein that the utility of dimebolins for treating epilepsy and epileptic syndromes may arise from one or more of its abilities to modulate the activity of AMPA and/or NMDA glutamate receptors (Grigorev et al., Bull Exp Biol Med., 136(5):474-477 (2003)), inhibit L-type calcium channels (Lermontova et al., Bulletin of Experimental Biology and Medicine, 132(5):1079-83 (2001)), block the action of neurotoxic beta-amyloid proteins, and/or block mitochondrial permeability transition pores (Bachurin et al., Annals of the New York Academy of Sciences, 993:334-344 (2003)), which are believed to play a role in the cell death that is associated with certain neurodegenerative diseases and aging in general. In particular, it is believed herein that glutamate receptors may play an important role in seizure initiation, maintenance and arrest. However, it is appreciated that blockade of all NMDA sites may have several unwanted side effects, such as has been observed with PCP narcotics. It is understood that retaining activity at selective and/or specific subunits is advantageous while at the same time modulating the activity of certain other AMPA and/or NMDA glutamate receptors.

In addition, compounds that have accompanying biochemical action may mitigate the effects of NMDA antagonism. For example, it has been discovered herein that dimebolins inhibit mitchrondrial permeability transition pores, and therefore may lead to protection of mitochondria from degradation.

Without being bound by theory, it is suggested that the anti-epileptic potential of a method of treatment or a pharmaceutical composition that includes one or more dimebolins, and/or pharmaceutically acceptable salts thereof, is not exclusively related to their anti-NMDA and/or NMDA antagonist activity. For example, a well known NMDA receptor antagonist is 2-amino-5-phosphonovaleric acid (AP5 or APV) (Evans et al., Brit. J. Pharmacol., 1982, v. 75, p. 65), and yet, AP5 has been reported to suffer from the disadvantage of having neurotoxic effects, including disturbance of coordination of movement and a sedative effect, each of which becomes apparent when AP5 is used in the doses in which it produces its anti-NMDA effect ($ED_{50}$=190 mg/kg, Grigoriev et al. Chim. Pharm. Journal, 1988, No. 3, p. 275-277). Accordingly, but without being bound by theory, it is believed herein that dimebolins exert selective action on NMDA sites. For example, dimebolins reportedly affect the polyamine site of NMDA-receptor located on the NR2B subunit, which is also the target for histamine (Grigorev et al., Bull Exp Biol Med, 136(5):474-7 (2003)). In addition, it has been reported that the H1-histamine receptor antagonist activity of dimebolins may also exert a modulating activity of NMDA-receptors by binding to that site. Thus, it has been discovered herein that the effect of dimebolins in low concentrations may be most pronounced in neuronal populations with high concentration of NR2B subunits. Such neuronal populations are primarily found in the fronto-parieto-temporal cortex and hippocampus pyramidal cells. It is understood herein that the temporal cortex and hippocampus are involved in the development of epilepsy, mainly of the temporal lobe subtype (McIntyre D C, et al. Epilepsia, 49 Suppl 3:23-30 (2008)).

It is also appreciated herein that epileptic activity results in $Ca^{2+}$ ion-dependent changes in mitochondrial function that might contribute to the neuronal injury induced by epilepsy (Kovács R, et al., J Neurosci., 25(17):4260-9 (2005)). Without being bound by theory, it is also believed herein that the efficacy of dimebolins may be due at least in part to their ability to block L-type calcium channels. Further, but without being bound by theory, it is believed herein that the efficacy of dimebolins may be due at least in part to their ability to inhibit mitochondrial permeability transition, a process involved in calcium-induced neurotoxicity, and can therefore be beneficial in the treatment of epilepsy. It is believed herein that inhibition of mitochondrial permeability transition pores decreases the damage caused during an epileptic seizure, especially the damage to cognitive function that may result.

Without being bound by theory, it is also believed herein that the pharmacokinetic characteristics and blood-brain-barrier permeability of dimebolins, in conjunction with a low number of adverse events reported in other therapies, are useful in treating epilepsy and epileptic syndromes according to the methods described herein. In contrast, many other NMDA antagonists have limited potential due at least in part to an unacceptable adverse prevent profile, such as has been reported for treatments including Aptiganel, Phencyclidine, and remacemide, unfavorable pharmacokinetic characteristics, such as with MRZ 2/596 and MDL 105,519, or reduced efficacy, such as with remacemide.

As used herein, the term "dimebolin" generally refers to the compounds described herein and analogs and derivatives thereof. It is also to be understood that in each of the foregoing, any corresponding pharmaceutically acceptable salt is also included in the illustrative embodiments described herein. Illustrative derivatives include, but are not limited to, both those compounds that may be synthetically prepared from the compounds described herein, as well as those compounds that may be prepared in a similar way as those described herein, but differing in the selection of starting materials. For example, described herein are illustrative dimebolins of formulae (I), (II), and (III) that include various functional groups on aromatic rings, such as $R^3$. It is to be understood that derivatives of those compounds also include the compounds having for example different functional groups on those aromatic rings than those explicitly set forth in the definition of formulae (I), (II), and (III). In addition, it is to be understood that derivatives of those compounds also include the compounds having those same or different functional groups at different positions on the aromatic ring. Similarly, derivatives include parallel variations of other functional groups on the compounds described herein, such as $R^1$, and the like.

Illustrative analogs include, but are not limited to, those compounds that share functional and in some cases structural similarity to those compounds described herein. For example, described herein are illustrative dimebolins of formulae (I), (II), and (III) that include a 2,3,4,5-tetrahydro-1H-pyridoindole ring system. Illustrative analogs include, but are not limited to, the corresponding ring expanded compounds, such as the corresponding azepinoindole ring system, and the like. Other illustrative analogs include, but are not limited to, the corresponding ring systems that include additional heteroatoms, such as the corresponding pyridazinoindole ring system, and the like.

Without being bound by theory, it is believed herein that one illustrative characteristic of the dimebolins, including analogs of the compounds described herein, is NMDA antagonism coupled with the ability to block L-type calcium channels. Without being bound by theory, it is believed herein that another illustrative characteristic of dimebolins, including analogs of the compounds described herein, is MPTP inhibition.

In addition, as used herein the term dimebolins also refers to prodrug derivatives of the compounds described herein, and including prodrugs of the various analogs and derivatives thereof. The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl ($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from 0, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

In addition, as used herein, the term dimebolins refers to both the amorphous as well as any and all morphological forms of each of the compounds described herein. In addition, as used herein, the term dimebolins refers to any and all hydrates, or other solvates, of the compounds described herein.

As used herein, the term "epilepsy" includes neurological disorders that are characterized by recurrent seizures. Such seizures may be transient signs and/or symptoms that arise due to abnormal, excessive or synchronous neuronal activity in the brain. Illustrative examples of epileptic seizures treatable with the methods and medicaments described herein include, but are not limited to, tonic-clonic, clonic (with or without tonic features), absence (typical or atypical), myoclonic absence, tonic, myoclonic, massive bilateral myoclonus, negative myoclonus, eyelid myclonia (accompanied or not by absence seizures), myoclonic-atonic, atonic, reflex, focal sensory (with elementary sensory symptoms, such as occipital and parietal lobe seizures, or experiential sensory symptoms, such as temporo parieto occipital junction seizures, and the like), focal motor (with elementary clonic motor signs, with asymmetrical tonic motor signs or seizure, such as supplementary motor seizures, with typical automatisms, also referred to as temporal lobe automatisms, such as mesial temporal lobe seizures, with hyperkinetic automatisms, with focal negative myoclonus, and the like), inhibitory motor, gelastic, hemiclonic, secondarily generalized, reflex seizures in focal epilepsy syndromes, generalized tonic-clonic status epilepticus, clonic status epilepticus, absence status epilepticus, tonic status epilepticus, myoclonic status epilepticus, epilepsia partialis continua, aura continua, limbic status epilepticus, hemiconvulsive status epilepticus.

It is appreciated that epilepsy may also occur in the context of one or more epileptic syndromes. Illustrative examples of epileptic syndromes treatable with the methods and medicaments described herein include, but are not limited to, benign familial neonatal seizures, early myoclonic encephalopathy, Ohtahara syndrome, migrating partial seizures of infancy, West syndrome, benign myoclonic epilepsy in infancy, benign familial and non-familial infantile seizures, Dravet's syndrome, HH syndrome, myoclonic status in nonprogressive encephalopathies, benign childhood epilepsy with centrotemporal spikes, early onset benign childhood occipital epilepsy (Panayiotopoulos type), late onset childhood occipital epilepsy (Gastaut type), epilepsy with myoclonic absences, epilepsy with myoclonic-astatic seizures, Lennox-Gastaut syndrome, Landau-Kleffner syndrome, epilepsy with continuous spike-and-waves during slow-wave sleep (other than LKS), childhood absence epilepsy, progressive myoclonus epilepsies, idiopathic generalized epilepsies with variable phenotypes (juvenile absence epilepsy, juvenile myoclonic epilepsy), reflex epilepsies, idiopathic photosensitive occipital lobe epilepsy, visual sensitive epilepsies, primary reading epilepsy, startle epilepsy, autosomal dominant nocturnal frontal lobe epilepsy, familial temporal lobe epilepsies, generalized epilepsies with febrile seizures plus, familial focal epilepsy with variable foci, limbic epilepsies, mesial temporal lobe epilepsy with hippocampal sclerosis, mesial temporal lobe epilepsy defined by specific etiologies, other types defined by location and etiology, neocortical epilepsies, Rasmussen syndrome, benign neonatal seizures, febrile seizures, reflex seizures, alcohol withdrawal seizures, drug or other chemically-induced seizures, immediate and early post traumatic seizures, single seizures or isolated clusters of seizures, and rarely repeated seizures (oligo-epilepsy).

In another embodiment, methods are described herein for treating Juvenile Myoclonic Epilepsy that include the step of administering a therapeutically effective amount of one or more dimebolins or pharmaceutically acceptable salts thereof. In another embodiment, methods are described herein for treating Juvenile Myoclonic Epilepsy that include the step of co-administering a therapeutically effective amount of one or more dimebolins or pharmaceutically acceptable salts thereof with a therapeutically effective amount of another subtype selective or subtype specific NMDA antagonists. In another embodiment, methods are described herein for treating Juvenile Myoclonic Epilepsy that include the step of co-administering a therapeutically effective amount of one or more dimebolins or pharmaceutically acceptable salts thereof with a therapeutically effective amount of one or more inhibitors of HMG-CoA reductase, also referred to as statins. In another embodiment, methods are described herein for treating Juvenile Myoclonic Epilepsy that include the step of co-administering a therapeutically effective amount of one or more dimebolins or pharmaceutically acceptable salts thereof with one or more GABA transaminase inhibitors. In another embodiment, methods are described herein for treating Juvenile Myoclonic Epilepsy that include the step of co-administering a therapeutically effective amount of one or more dimebolins or pharmaceutically acceptable salts thereof with one or more T-Type Calcium Channel inhibitors. In another embodiment, methods are described herein for treating Juvenile Myoclonic Epilepsy that include the step of co-administering a therapeutically effective amount of one or more dimebolins or pharmaceutically acceptable salts thereof with one or more statins and one or more GABA transaminase inhibitors.

In another embodiment, methods are described herein for treating epilepsy or epileptic syndromes that include the step of administering a therapeutically effective amount of one or more dimebolins of formula (I)

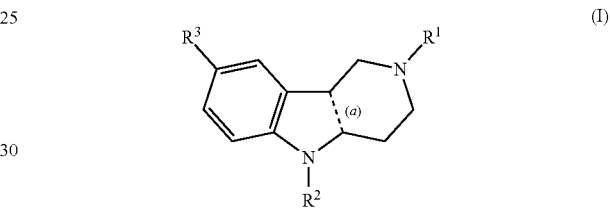

or a pharmaceutically acceptable salt thereof, wherein $R^1$ is alkyl or arylalkyl; $R^2$ is hydrogen, benzyl, or 6-methylpyridinyl-3-ethyl; $R^3$ is hydrogen, alkyl, or halo; and bond (a) is a single bond or a double bond.

In another embodiment, methods are described herein that include the step of administering a therapeutically effective amount of a dimebolin of formula (I) wherein $R^1$ is methyl, ethyl or benzyl. In another embodiment, methods are described herein that include the step of administering a therapeutically effective amount of a dimebolin of formula (I) wherein $R^2$ is hydrogen, benzyl, or 6-methylpyridinyl-3-ethyl. In another embodiment, methods are described herein that include the step of administering a therapeutically effective amount of a dimebolin of formula (I) wherein $R^3$ is hydrogen, methyl, or bromo.

In another embodiment, methods are described herein for treating epilepsy and epileptic syndromes that include the step of administering a therapeutically effective amount of a dimebolin of formula (I) wherein bond (a) is a single bond; $R^1$ and $R^3$ are each methyl; and $R^2$ is hydrogen. In another embodiment, methods are described herein that include the step of administering a therapeutically effective amount of a dimebolin of formula (I) wherein bond (a) is a single bond; and the ring fusion is cis. In another embodiment, methods are described herein that include the step of administering a therapeutically effective amount of a dimebolin of formula (I) wherein bond (a) is a double bond; $R^1$ is ethyl or benzyl; and $R^2$ and $R^3$ are each hydrogen; or $R^1$ and $R^3$ are each methyl; and $R^2$ is benzyl; or $R^1$ is methyl; $R^2$ is 6-methylpyridinyl-3-ethyl; and $R^3$ is hydrogen; or $R^1$ and $R^3$ are each methyl; and $R^2$ is 6-methylpyridinyl-3-ethyl; or $R^1$ is methyl; $R^2$ is hydrogen; and $R^3$ is hydrogen or methyl; or $R^1$ is methyl; $R^2$ is hydrogen; and $R^3$ is bromo.

In another embodiment, methods are described herein for treating epilepsy and epileptic syndromes that include the step of administering a therapeutically effective amount of one or more dimebolins of formula (II)

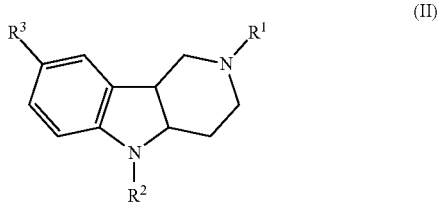

(II)

or a pharmaceutically acceptable salt thereof, wherein $R^1$ is alkyl or arylalkyl; $R^2$ is hydrogen, benzyl, or 6-methylpyridinyl-3-ethyl; $R^3$ is hydrogen, alkyl, or halo; and bond (a) is a single bond or a double bond.

In another embodiment, methods are described herein for treating epilepsy and epileptic syndromes that include the step of administering a therapeutically effective amount of a dimebolin of formula (II) wherein $R^1$ is methyl, ethyl or benzyl. In another embodiment, methods are described herein that include the step of administering a therapeutically effective amount of a dimebolin of formula (II) wherein $R^2$ is hydrogen, benzyl, or 6-methylpyridinyl-3-ethyl. In another embodiment, methods are described herein that include the step of administering a therapeutically effective amount of a dimebolin of formula (II) wherein $R^3$ is hydrogen, methyl, or bromo. In another embodiment, methods are described herein include the step of administering a therapeutically effective amount of a dimebolin of formula (II) wherein $R^1$ and $R^3$ are each methyl; and $R^2$ is hydrogen. In another embodiment, methods are described herein that include the step of administering a therapeutically effective amount of a dimebolin of formula (II) wherein the ring fusion is cis. In another embodiment, methods are described herein that include the step of administering a therapeutically effective amount of a dimebolin of formula (II) in a pharmaceutically acceptable quaternary salt form.

In another embodiment, methods are described herein for treating epilepsy and epileptic syndromes that include the step of administering a therapeutically effective amount of one or more dimebolins of formula (III)

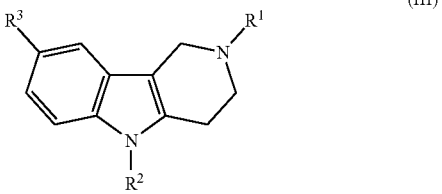

(III)

or a pharmaceutically acceptable salt thereof, wherein $R^1$ is alkyl or arylalkyl; $R^2$ is hydrogen, benzyl, or 6-methylpyridinyl-3-ethyl; $R^3$ is hydrogen, alkyl, or halo; and bond (a) is a single bond or a double bond.

In another embodiment, methods are described herein for treating epilepsy and epileptic syndromes that include the step of administering a therapeutically effective amount of one or more dimebolins of formula (III) wherein $R^1$ is methyl, ethyl or benzyl. In another embodiment, methods are described herein that include the step of administering a therapeutically effective amount of one or more dimebolins of formula (III) wherein $R^2$ is hydrogen, benzyl, or 6-methylpyridinyl-3-ethyl. In another embodiment, methods are described herein that include the step of administering a therapeutically effective amount of one or more dimebolins of formula (III) wherein $R^3$ is hydrogen, methyl, or bromo.

In another embodiment, methods are described herein for treating epilepsy and epileptic syndromes that include the step of administering a therapeutically effective amount of one or more dimebolins of formula (III) wherein $R^1$ is ethyl or benzyl; and $R^2$ and $R^3$ are each hydrogen; or $R^1$ and $R^3$ are each methyl; and $R^2$ is benzyl; or $R^1$ is methyl; $R^2$ is 6-methylpyridinyl-3-ethyl; and $R^3$ is hydrogen; or $R^1$ and $R^3$ are each methyl; and $R^2$ is 6-methylpyridinyl-3-ethyl; or $R^1$ is methyl; $R^2$ is hydrogen; and $R^3$ is hydrogen or methyl; or $R^1$ is methyl; $R^2$ is hydrogen; and $R^3$ is bromo. In another embodiment, methods are described herein that include the step of administering a therapeutically effective amount of one or more dimebolins of formula (III) in a pharmaceutically acceptable quaternary salt form.

In another embodiment, methods are described herein for treating epilepsy and epileptic syndromes that include the step of administering a therapeutically effective amount of a dimebolin of the formula

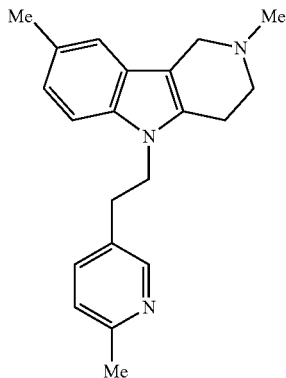 [SMILES: Cc1ccc2c(c1)c1c(n2CCc2ccc(C)nc2)CCN(C)C1]

or a pharmaceutically acceptable salt, such as the hydrochloride salt.

In another embodiment, methods are described herein for treating epilepsy and epileptic syndromes that include the step of administering a therapeutically effective amount of one or more compounds selected from 2-methyl-2,3,4,5-tetrahydro-1H-pyrido[4,3-b]indole; 2,8-dimethyl-2,3,4,5-tetrahydro-1H-pyrido[4,3-b]indole, or its methyliodide; cis-(±) 2,8-dimethyl-2,3,4,4a,5,9b-hexahydro1H-pyrido[4,3-b]indole, or its dihydrochloride; 2-methyl-8-bromo-2,3,4,5-tetrahydro-1H-pyrido[4,3-b]indole, or its hydrochloride; 2-ethyl-2,3,4,5-tetrahydro-1H-pyrido[4,3-b]indole; 2-benzyl-2,3,4,5-tetrahydro-1H-pyrido[4,3-b]indole; 2,8-dimethyl-5-benzyl-2,3,4,5-tetrahydro-1H-pyrido[4,3-b]indole, or its hydrochloride; 2-methyl-5-[2-(6-methyl-3-pyridyl) ethyl]-2,3,4,5-tetrahydro-1H-pyrido[4,3-b]indole, or its sesquisulfate monohydrate; and 2,8-dimethyl-5-[2-(6-methyl-3-pyridyl)ethyl]-2,3,4,5-tetrahydro-1H-pyrido[4,3-b]indole, or its dihydrochloride. The foregoing compounds may be prepared according to Horlein, Chem. Ber., 1954, Bd.87, hft 4, p. 463-472; Cattanach et al., J. Chem. Soc. (ser. C) 1968, 1235-1243; Yurovskaya and Rodionov, Khim. Geterots. Soed., 1981, No. 8, p. 1072-1078; Yakhontov and Glushkova, Synthatic Drugs (edited by A. G. Natradze), Moscow, "Meditsina Publishers", 1983, p. 234-237; Buu-Hoi et al., J. Chem. Soc., 1964, No. 2, p. 708-711; Kucherova and Kochetkov, J. Obshch. Khim., 1956, v. 26, p. 3149-3154; and Kost et al., "Khim. Geterots. Soed.", 1973, No. 2, p. 207-212, the disclosure of which are incorporated herein by reference.

In another embodiment, one or more dimebolins or pharmaceutically acceptable salts thereof is co-administered with another NMDA antagonist, such as a subtype selective or subtype specific NMDA antagonist. In another embodiment, one or more dimebolins or pharmaceutically acceptable salts thereof is co-administered with another AMPA antagonist, such as a subtype selective or subtype specific AMPA antagonist. Glutamate receptors bind glutamate, an excitatory amino acid neurotransmitter. Upon binding glutamate, the receptors facilitate the flow of both sodium and calcium ions into the cell, while potassium ions flow out of the cell, resulting in excitation. The glutamate receptor has 5 potential binding sites and causes different responses depending on the stimulated or blocked site. These sites are the alpha-amino-3-hydroxy-5-methylisoxazole-4-propionic acid (AMPA) site, the kainate site, the N-methyl-D-aspartate (NMDA) site, the glycine site, and the metabotropic site that has 7 subunits (GluR 1-7). AEDs that modify these receptors are antagonistic to glutamate.

Illustrative NMDA antagonists include, but are not limited to amantadine, dextromethorphan, dextrorphan, ibogaine, ketamine, phencyclidine, riluzole, tiletamine. memantine (also known as AXURA, AKATINOL, NAMENDA, EBIXA, and 1-amino-3,5-dimethyladamantane). In another embodiment, one or more dimebolins or pharmaceutically acceptable salts thereof is co-administered with one or more of riluzole, memantine, and dextromethorphan, and therapeutically active and pharmaceutically acceptable salt derivatives thereof, including acid addition salt forms. In another embodiment, one or more dimebolins or pharmaceutically acceptable salts thereof is co-administered with memantine.

In another embodiment, one or more dimebolins or pharmaceutically acceptable salts thereof is co-administered with another NMDA antagonist, such as an noncompetitive antagonist, including but not limited to Dizocilpine (also known as MK-801), aptiganel (also known as CERESTAT, CNS-1102), remacimide, and HU-211. In another embodiment, one or more dimebolins or pharmaceutically acceptable salts thereof is co-administered with HU-211.

In another embodiment, one or more dimebolins or pharmaceutically acceptable salts thereof is co-administered with another NMDA antagonist, such as a glycine antagonist that acts at the glycine binding site, including but not limited to 7-chlorokynurenate, 5,7-dichlorokynurenic acid (DCKA), kynurenic acid, and 1-aminocyclopropanecarboxylic acid (ACPC).

In another embodiment, one or more dimebolins or pharmaceutically acceptable salts thereof is co-administered with another NMDA antagonist, such as a competitive antagonist, including but not limited to 2-amino-7-phosphonoheptanoic acid (AP7), R-2-amino-5-phosphonopentanoate (APV), and CPPene (3-[(R)-2-carboxypiperazin-4-yl]-prop-2-enyl-1-phosphonic acid).

In another embodiment, one or more dimebolins or pharmaceutically acceptable salts thereof is co-administered with another anti-epileptic drug (AED). Illustrative AEDs may be grouped according to their main mechanism of action, although it is to be understood that such a classification is not be interpreted as limiting because many AEDs have been reported to operate by more than one mode of action. The majority of modes of action reported as possible bases of the efficacy of AEDs, include sodium channel blockers, calcium current inhibitors, gamma-aminobutyric acid (GABA) enhancers, glutamate blockers, carbonic anhydrase inhibitors, and hormones (Ochoa et al., "Antiepileptic Drugs: An Overview" emedicine from WebMD (Apr. 17, 2009)).

Illustrative anti-epileptic drugs include, but are not limited to acetazolamide, acetazolamide modified release, barbexaclone, breveracetam, carbamazepine, carbamazepine modified release, clobazam, clonazepam, clorazepate, diazepam, ethosuximide, ethotoin, felbamate, gabapentin, lamotrigine, levetiracetam, lorazepam, mephenytoin, mesuximide, methazolamide, methylphenobarbital, oxcarbamazepine, phenobarbital (phenobarbitone), phensuximide, phenytoin, pregabalin, primidone, progabide, seletracetam, rufinamide, valproic acid, sodium valproate, divalproate sodium, sodium valproate modified release, tiagabine, topiramate, vigabatrin, and zonisamide, including sustained released zonisamide.

In another embodiment, one or more dimebolins or pharmaceutically acceptable salts thereof is co-administered with a voltage-gated sodium channel antagonist, such as with oxcarbamazepine. For example, it has been reported that the firing of an action potential by an axon is accomplished through sodium channels. Each sodium channel dynamically exists in 3 states, as follows: a resting state during which the channel allows passage of sodium into the cell; an active state in which the channel allows increased influx of sodium into the cell; and an inactive state in which the channel does not allow passage of sodium into the cell. During an action potential, these channels exist in the active state and allow influx of sodium ions. Once the activation or stimulus is terminated, a percentage of these sodium channels become inactive for a period of time known as the refractory period. With constant stimulus or rapid firing, many of these channels exist in the inactive state, rendering the axon incapable of propagating the action potential. AEDs that target these sodium channels may prevent the return of these channels to the active state by stabilizing the inactive form of these channels. In doing so, repetitive firing of the axons is prevented.

In another embodiment, one or more dimebolins or pharmaceutically acceptable salts thereof is co-administered with a voltage-dependent calcium channel blockers, such as an L-type channel blocker. Illustrative calcium channel blockers include, but are not limited to, oxcarbamazepine. While the mode of action of several AEDs includes the modification of glutamate receptors (Sierra-Paredes and Sierra-Marcuno, Extrasynaptic GABA and glutamate receptors in epilepsy, CNS Neurol Disord Drug Targets, 6(4):288-300 (2007); Nateri et al., EMBO J., 2007 Nov. 28, 26(23): 4891-901 Epub 2007 Nov. 1)), inhibition of voltage-dependent calcium channels (VDCC) has been reported to mediate the effects of those and other AEDs. Calcium channels have been reported to exist in 3 known forms in the human brain, namely the L, N, and T forms. These channels are small and are inactivated quickly. The influx of calcium currents in the resting state produces a partial depolarization of the membrane, facilitating the development of an action potential after rapid depolarization of the cell. They function as the pacemakers of normal rhythmic brain activity. This is true particularly of the thalamus. T-form calcium channels have been known to play a role in the 3 per second spike-and-wave discharges of absence seizures. Anti-epileptic drugs that inhibit these T-calcium channels have been reported to be particularly useful for controlling absence seizures.

In another embodiment, one or more dimebolins or pharmaceutically acceptable salts thereof is co-administered with a GABA mimetic or GABA agonist. Illustrative GABA mimetics include, but are not limited to tiagabine, vigabatrin, and the like. Without being bound by theory, it is believed herein that when GABA binds to a GABA-A receptor, the passage of chloride, a negatively charged ion, into the cell is facilitated via chloride channels. This influx of chloride increases the negativity of the cell, resulting in a more negative resting membrane potential. This negativity causes the cell to have greater difficulty reaching the action potential. GABA is produced by decarboxylation of glutamate mediated by the enzyme glutamic acid decarboxylase (GAD). Certain AEDs have been reported to act as modulators of this enzyme, enhancing the production of GABA and down-regulating glutamate. Other AEDs may function as an agonist to this mode of chloride conductance by blocking the reuptake of GABA, such as the drug tiagabine, or alternatively by inhibiting its metabolism mediated by GABA transaminase, such as the drug vigabatrin, resulting in increased accumulation of GABA at the postsynaptic receptors.

In another embodiment, methods are described herein for treating epilepsy and epileptic syndromes that include the step of co-administering a therapeutically effective amount of one or more dimebolins or pharmaceutically acceptable salts thereof with one or more GABA transaminase inhibitors. In another embodiment, methods are described herein that include the step of co-administering a therapeutically effective amount of one or more dimebolins or pharmaceutically acceptable salts thereof with one or more T-Type Calcium Channel inhibitors.

Other AEDs have been reported to exert efficacy by inhibition of the enzyme carbonic anhydrase, which increases the concentration of hydrogen ions intracellularly and decreases the pH. The potassium ions shift to the extracellular compartment to buffer the acid-base status. This event results in hyperpolarization and an increase in seizure threshold of the cells. Acetazolamide, an inhibitor of carbonic anhydrase, has been used as an adjunctive therapy in refractory seizures with catamenial pattern, such as seizure clustering around menstrual period. Topiramate and zonisamide also are weak inhibitors of this enzyme; however, that activity is not believed to be an important mechanism for their observed antiseizure efficacy. Other AEDs have been reported to mimic the activity of certain sex hormones. For example, progesterone is a natural anticonvulsant that acts by increasing chloride conductance at GABA-A receptors and attenuates glutamate excitatory response. It also alters messenger RNA for GAD and GABA-A receptor subunits. In contrast, estrogen acts as a pro-convulsant by reducing chloride conductance and acting as an agonist at NMDA receptors in the CA1 region of the hippocampus. In another illustrative embodiment, one or more dimebolins or pharmaceutically acceptable salts thereof is co-administered with one or more of each of the foregoing AEDs.

In another illustrative embodiment, one or more dimebolins or pharmaceutically acceptable salts thereof is co-administered with one or more GABA agonists, such as valproic acid, sodium valproate, divalproate sodium, sodium valproate modified release, tiagabine, and topiramate. In another embodiment, one or more dimebolins or pharmaceutically acceptable salts thereof is co-administered with sodium valproate. In another illustrative embodiment, one or more dimebolins or pharmaceutically acceptable salts thereof is co-administered with one or more barbiturates. It is appreciated that ordinarily barbiturates have not been extensively used due to the higher propensity for adverse events observed with those drugs. Even so, but without being bound by theory, when used as a co-therapy as described herein, it is appreciated herein that lower doses may be used in conjunction with the one or more dimebolins or pharmaceutically acceptable salts thereof, leading to an improved therapeutic window.

In another embodiment, methods are described herein for treating epilepsy and epileptic syndromes that include the step of co-administering a therapeutically effective amount of one or more dimebolins or pharmaceutically acceptable salts thereof with one or more inhibitors of HMG-CoA reductase, also referred to as statins. Illustrative statins include simvastatin, pravastatin, lovastatin, fluvastatin, atorvastatin, rosuvastatin or cerivastatin, or a pharmaceutically acceptable salt thereof, including therapeutically effective acid addition salt forms of any of the foregoing. In another embodiment, one or more dimebolins or pharmaceutically acceptable salts thereof is co-administered with simvastatin. In another embodiment, one or more dimebolins or pharmaceutically acceptable salts thereof is co-administered with simvastatin and sodium valproate. In another embodiment, methods are described herein that include the step of co-administering a therapeutically effective amount of one or more dimebolins or pharmaceutically acceptable salts thereof with one or more statins and one or more GABA transaminase inhibitors.

It is to be understood that in any of the embodiments described herein, the corresponding acid addition salt may be administered. Illustrative acid salts may be formed from, but at not limited to, inorganic acids such as hydrohalic acids, including hydrochloric or hydrobromic acid; sulfuric; nitric; phosphoric, and the like acids; and organic acids such as acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In addition, in those embodiments described herein drawn to combination therapy comprising administration of one or more dimebolins or pharmaceutically acceptable salts thereof and one or more NMDA antagonists and/or one or more anti-epileptic drugs, "therapeutically effective amount" refers to that amount of the combination of agents taken together so that the combined effect elicits the desired biological or medicinal response. For example, the therapeutically effective amount combinations or co-administered compounds and compositions, such as of dimebon and topiramate, dimebon and simvastatin, and the like, would illustratively be the amount of dimebon and the amount of topiramate, or the amount of dimebon and the amount of the simvastatin, and the like that when taken together or sequentially have a combined effect that is therapeutically effective. Further, it is appreciated that in some embodiments of such methods that include co-administration, the amount of dimebon, topiramate, and/or simvastatin, and the like when taken individually may or may not be therapeutically effective.

In addition, in those embodiments described herein drawn to combination therapy, "therapeutically effective amount" refers to that amount of the combination of agents taken together so that the combined effect elicits the desired biological or medicinal response. For example, the therapeutically effective amount of one or more dimebolins and one or more additional subtype selective or subtype specific NMDA antagonists, would be the amount of each component that when taken together or sequentially have a combined effect that is therapeutically effective. Further, it is appreciated that in some embodiments of such methods that include co-administration, that co-administration amount of for example one or more dimebolins and one or more additional subtype selective or subtype specific NMDA antagonists, when taken individually may or may not be therapeutically effective.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

Accordingly, in another illustrative embodiment, the amounts of the one or more NMDA receptor antagonists that are administered to the patient in the methods described herein are equal to or less than those that are given in conventional monotherapy using such NMDA receptor antagonists. In another illustrative embodiment, the amounts of the anti-epileptic drugs that are administered to the patient in the methods described are equal to or less than those that are given in conventional monotherapy using such anti-epileptic drugs.

In another illustrative embodiment where either or both of an NMDA receptor antagonist and/or a anti-epileptic drug are co-administered with one or more dimebolins or pharmaceutically acceptable salts thereof, co-administration includes dosing protocols where the two or more compounds are given simultaneously or contemporaneously. It is to be understood that co-administration is not limited to any particular time frame. For example, dosing protocols where one or more dimebolins or pharmaceutically acceptable salts thereof are given every other day, and the NMDA antagonist is given on the alternate days that the dimebolins are not given are included in the co-administration methods described herein.

In another embodiment, the therapeutically effective amount of the one or more dimebolins is an amount capable of antagonizing NMDA receptors and blocking calcium channels, such as L-type calcium channels. In one variation, the therapeutically effective amount is capable of only blocking selected subtypes of NMDA receptors and blocking calcium channels, such as L-type calcium channels. In another embodiment, the therapeutically effective amount of the one or more dimebolins is an amount capable of inhibiting or blocking mitochondrial permeability transition pores. In another embodiment, the therapeutically effective amount of the one or more dimebolins is an amount capable of antagonizing NMDA receptors and blocking calcium channels, such as L-type calcium channels, and inhibiting or blocking mitochondrial permeability transition pores.

As used herein, the term "composition" generally refers to any product comprising the specified ingredients in the specified amounts, as well as any product which results, directly or indirectly, from combinations of the specified ingredients in the specified amounts. Illustratively, compositions may include one or more carriers, diluents, and/or excipients. The compounds described herein may be formulated in a therapeutically effective amount in conventional dosage forms for the methods described herein, including one or more carriers, diluents, and/or excipients therefor. Such formulation compositions may be administered by a wide variety of conventional routes for the methods described herein in a wide variety of dosage formats, utilizing art-recognized products. See generally, Remington's Pharmaceutical Sciences, (16th ed. 1980). It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens.

Examples of illustrative methods of administration include, but are not limited to, oral (po), intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or pen-spinal routes of administration by delivery via intracranial or intravertebral needles and/or catheters with or without pump devices. It is to be understood that in the methods described herein that include co-administration of one or more dimebolins or pharmaceutically acceptable salts thereof, the individual components of a co-administration, or combination can be administered by any suitable means, simultaneously, sequentially, separately or in a single pharmaceutical formulation. Where the one or more dimebolins, the NMDA receptor antagonists and the anti-epileptic drugs are administered in separate dosage forms, the number of dosages administered per day for each compound may be the same or different. Dimebolins, and optionally the NMDA receptor antagonists and/or the anti-epileptic drugs may be administered via the same or different routes of administration. Dimebolins, and optionally the NMDA receptor antagonists and/or the anti-epileptic drugs may be administered according to simultaneous or alternating regimens, at the same or different times during the course of the therapy, concurrently in divided or single forms.

It is to be understood that a wide range of doses of one or more dimebolins or pharmaceutically acceptable salts thereof, either alone or in combination with another component, may be used in the methods and compositions described herein. In addition, any suitable route of administration may be used in the methods described herein. In addition, any suitable formulation may be used for the compositions described herein. In another illustrative embodiment, oral formulations of one or more dimebolins or pharmaceutically acceptable salts thereof, either alone or in combination with another component, are described. In another illustrative embodiment, parenteral formulations of one or more dimebolins or pharmaceutically acceptable salts thereof, either alone or in combination with another component, are described.

In another embodiment, the methods described herein include the use of controlled release and/or slow release formulations of the compounds and/or combination of compounds described herein are described. It is appreciated that a controlled release and/or slow release formulation of one or more dimebolins or pharmaceutically acceptable salts thereof, may be advantageous for maintaining therapeutically effective blood levels in between doses. In another embodiment, formulations suitable for parenteral administration are described herein, including formulations suitable for pumps and or patches that may be adhered to or worn by a patient.

In another illustrative embodiment of the methods described herein, one or more dimebolins or pharmaceutically acceptable salts thereof, described herein is illustratively administered to a patient orally in the range from about 0.1 mg/kg to about 1 g/kg, from about 0.1 mg/kg to about 1 mg/kg, from about 0.1 mg/kg to about 10 mg/kg, from about 1 mg/kg to about 10 mg/kg, from about 1 mg/kg to about 100 mg/kg, from about 1 mg/kg to about 200 mg/kg, from about 1 mg/kg to about 500 mg/kg, from about 1 mg/kg to about 1 g/kg, from about 10 mg/kg to about 100 mg/kg, from about 10 mg/kg to about 200 mg/kg, from about 10 mg/kg to about 500 mg/kg, from about 10 mg/kg to about 1 g/kg, from about 20 mg/kg to about 50 mg/kg, from about 20 mg/kg to about 100 mg/kg, from about 20 mg/kg to about 200 mg/kg, from about 50 mg/kg to about 100 mg/kg, from about 50 mg/kg to about 200 mg/kg, from about 100 mg/kg to about 200 mg/kg, from about 100 mg/kg to about 500 mg/kg, or from about 100 mg/kg to about 1 g/kg, where the dose corresponds to the total of the one or more dimebolins. It is also appreciated that when used in combination with other compounds described herein, such as with one or more NMDA receptor antagonists, and/or one or more statins, and/or one or more AEDs, the lower dose ranges may be illustratively used.

In another illustrative embodiment of the methods described herein, one or more dimebolins or pharmaceutically acceptable salts thereof, described herein is illustratively administered to a patient parenterally in the range from about 0.1 mg/kg to about 1 g/kg, from about 0.1 mg/kg to about 1 mg/kg, from about 0.1 mg/kg to about 10 mg/kg, from about 1 mg/kg to about 10 mg/kg, from about 1 mg/kg to about 100 mg/kg, from about 1 mg/kg to about 200 mg/kg, from about 1 mg/kg to about 500 mg/kg, from about 1 mg/kg to about 1 g/kg, from about 10 mg/kg to about 100 mg/kg, from about 10 mg/kg to about 200 mg/kg, from about 10 mg/kg to about 500 mg/kg, from about 10 mg/kg to about 1 g/kg, from about 20 mg/kg to about 50 mg/kg, from about 20 mg/kg to about 100 mg/kg, from about 20 mg/kg to about 200 mg/kg, from about 50 mg/kg to about 100 mg/kg, from about 50 mg/kg to about 200 mg/kg, from about 100 mg/kg to about 200 mg/kg, from about 100 mg/kg to about 500 mg/kg, or from about 100 mg/kg to about 1 g/kg, where the dose corresponds to the total of the one or more dimebolins. It is also appreciated that when used in combination with other compounds described herein, such as with one or more NMDA receptor antagonists, and/or one or more statins, and/or one or more AEDs, the lower dose ranges may be illustratively used.

In another embodiment, when used alone or in combination, one or more dimebolins or pharmaceutically acceptable salts thereof, are administered orally to a patient at a daily dose of 0.1, 0.5, 1.0, 2.0, or 5.0 mg/kg, corresponding to approximately, 6.0, 30, 60, 120, or 300 mg for an average weight adult. Without limiting the foregoing, it is appreciated that such lower doses of dimebolins may be more applicable to an ongoing, or chronic therapy, designed for continuous administration, rather than intermittent or acute administration. Accordingly, the daily dose may be divided and administered b.i.d. and/or t.i.d, although it is to be understood that q.d. dosing is described herein.

It is to be understood that the illustrative doses described herein represent daily doses, and may be therefore administered q.d., b.i.d., t.i.d., and according to additional dosing protocols. In addition, it is to be understood that the doses may be single or divided.

It is appreciated that when used in combination with other compounds described herein, such as with one or more NMDA receptor antagonists, and/or one or more statins, and/or one or more AEDs, the lower dose ranges may be illustratively used. It is further appreciated that as described herein that one or more dimebolins or pharmaceutically acceptable salts thereof, may be efficacious within two or more distinct dosing windows. It has been discovered herein that because dimebolins efficaciously operate via multiple mechanisms, dimebolins may be efficacious by a first mechanism of action at a lower dose, and also efficacious by a second mechanism of action at a higher dose.

Accordingly, also described herein are unitary dosage forms for oral administration that include a low dose of one or more dimebolins or pharmaceutically acceptable salts thereof, such as 5 mg or 10 mg of a total of one or more dimebolins, and one or more pharmaceutically acceptable carriers, diluents, or excipients. Illustratively, the unitary dosage forms are tablets or capsules.

In another embodiment, the methods described herein include the use of tablets for pediatric use. It is appreciated that pediatric dosages may not be linearly related to adult doses on a mg/kg basis. Illustratively, pediatric doses of dimebolins are described herein, such as oral doses that include 2 mg, 2.5 mg, 3 mg, 5 mg, 10 mg, or 15 mg, each of which may be administered q.d., b.i.d., t.i.d., or according to additional dosing protocols, and be in a single or divided unitary dose format.

In one variation of each of the foregoing embodiments, the one or more dimebolins or pharmaceutically acceptable salts thereof, are administered t.i.d.

In another embodiment, chronic dosing protocols are described for the methods described herein. In one aspect, one or more dimebolins or pharmaceutically acceptable salts thereof, is administered to a patient in need of relief from epilepsy on a continuous basis whether or not the patient is showing any signs or symptoms of epilepsy. Illustratively, the dose administered is selected from the lower ranges of dosing described herein. In another embodiment, acute dosing protocols are described for the methods described herein. In one aspect, one or more dimebolins or pharmaceutically acceptable salts thereof, is administered to a patient in need of relief from epilepsy on an intermittent basis, as determined by recent or anticipated signs or symptoms of epilepsy. Illustratively, the dose administered is selected from the higher ranges of dosing described herein.

In another embodiment, when used alone or in combination, one or more dimebolins or pharmaceutically acceptable salts thereof, are administered intravenously to a patient at a daily dose of 5.0, 10, 15, 20, 25, or 30 mg/kg, corresponding to approximately 300, 600, 900, 1200, 1500, or 1800 mg for an average weight adult. Without limiting the foregoing, it is appreciated that such higher doses of dimebolins may be more applicable to an acute therapy, such as in a rescue or emergency situation, rather than an ongoing, or chronic therapy.

In another embodiment, the methods described herein include a titration step where the dose is gradually increased over a predetermined time period, such as a two step protocol for adults as follows: 2 mg thrice daily for 7 days, then 5 mg thrice daily, 5 mg thrice daily for 7 days, then 10 mg thrice daily, or 10 mg thrice daily for 7 days, then 20 mg thrice daily.

In another embodiment, process for making pharmaceutical compositions are described herein. The processes include the step of adapting the one or more dimebolins and the one or more NMDA receptor antagonists, or pharmaceutically acceptable salts of the foregoing, for co-administration. In another embodiment, the processes include the step of adapting the one or more dimebolins and the one or more other anti-epileptic drugs, or pharmaceutically acceptable salts of the foregoing, for co-administration. In another embodiment, the processes include the step of adapting the one or more dimebolins, the one or more other anti-epileptic drugs, and the one or more NMDA receptor antagonists, or pharmaceutically acceptable salts of the foregoing, for co-administration.

In another embodiment, pharmaceutical composition packages are described herein. In one embodiment, the package includes a therapeutically effective amount of one or more dimebolins and a therapeutically effective amount of one or more NMDA receptor antagonists, or pharmaceutically acceptable salts of the foregoing, each adapted for co-administration. In another embodiment, the package includes a therapeutically effective amount of one or more dimebolins and a therapeutically effective amount of one or more other anti-epileptic drugs, or pharmaceutically acceptable salts of the foregoing; each adapted for co-administration. In another embodiment, the package includes a therapeutically effective amount of one or more dimebolins, a therapeutically effective amount of one or more NMDA receptor antagonists, and a therapeutically effective amount of one or more NMDA receptor antagonists, or pharmaceutically acceptable salts of the foregoing, each adapted for co-administration.

It is to be understood that in each of the foregoing embodiments of the methods and medicaments described herein, any one or more of the dimebolins may be included therein. For example, in each of the foregoing embodiments of the methods and medicaments described herein, the dimebolin may be dimebon (dimebolin hydrochloride), or other pharmaceutically acceptable salt thereof.

The effective use of the methods described herein for treating or ameliorating one or more effects of a epilepsy or epileptic syndromes using one or more compounds described herein may be based upon animal models, such as murine and rabbit models. For example, it is understood that epilepsy and/or epileptic syndromes in humans are characterized by a loss of function, and/or the development of symptoms, each of which may be elicited in animals, such as mice and rabbits, and other surrogate test animals. Illustrative models that may be used to evaluate the methods of treatment and the pharmaceutical compositions described herein to determine the therapeutically effective amounts described herein, include the rabbit anti-GluR3 antibody model, rat global hypoxia model, rat hyperthermia-induced model, baboon or cat GABA withdrawal, tetanus toxin model, mouse cystatin B-deficient model, beagle or rat lateral fluid—percussion injury model, baboon, chicken or rat/hot water model, rat or mouse GEPRs, DBA/2 mouse model, mouse EL mouse model, rat tish mutation model, mouse GABA receptor b3 knockout model, TNAP-deficient mouse model (BALBc mice), macular mutant mouse model, twitcher mouse model, mouse ethanol withdrawal model, the JNK3 homozygous (−/−) knockout mouse model, and the mouse, rat, or rabbit cocaine-induced model, the descriptions are which are described by Sarkisian, Epilepsy & Behavior 2, 201-216 (2001), and references therein, the disclosure of which is incorporated herein by reference.

The following examples further illustrate specific embodiments of the invention; however, the following illustrative examples should not be interpreted in any way to are to limit invention.

EXAMPLES

Example

Kainic acid or Pilocarpine Induced Kindling Model in Rats. One or more dimebolins are shown to be efficacious in the rat. Briefly, compounds described herein are administered to male CD rats at 10 mg/kg intravenously through a tail vein catheter, followed immediately by a 30 mg/kg subcutaneous injection. Vehicle controls receive the same injection volumes of the PPCES vehicle alone. Thirty minutes later, animals are given a 1-mg/kg i.p. injection of kainic acid in normal saline solution (a dose of kainic acid that has been previously reported to induce a seizure syndrome in rats, Maj et al., Eur. J. Pharm. 359:27 32, 1992). Seizure behavior is monitored for 4 hours following kainic acid injection. Behaviors are assessed based on the following cumulative scoring system: 1 pt.=arrest of motion; 2 pts.=myoclonic jerks of the head and neck (moderate); 3 pts.=unilateral or bilateral forelimb clonic activity; 4 pts.=whole body clonus; 5 pts.=clonic-tonic seizures; 6 pts.=status epilepticus (see also Mathis and Ungerer, Exp. Brain Res. 88:277 282, 1992; Rong et al., Proc. Natl. Acad. Sci. USA 96:9897 9902, 1999; Yang et al., Nature 389:865 870, 1997, Muller-Schwarz et al., Neuroreport, vol. 10, No. 7, 1999, pp. 1517-1522; Ebert et al. Epilepsia 2002, 43 Suppl 5, 86-95; Tober et al. European Journal of Pharmacology 1996, 303, 163-169; Clifford et al, "Effect of anticonvulsant drugs on kainic acid induced epileptiform activity," Exp. Neurol. 76: 156 (1982)).

Example

Chronic Anticonvulsant Activity Using the Kainic Acid Seizure Test in Rat. Dimebolins, including the compounds described herein, are shown to be efficacious in the rat kainic acid anticonvulsant activity model. It is appreciated that this model, though general, may also most closely correspond to and/or be more predictive of temporal lobe epilepsy found in humans. However, it is to be understood that this model is a general surrogate for all types of epilepsy.

Male Wistar rats (such as Male Rj: Wistar (Han) rats, weighing 180-280 g at the day of testing, from Elevage Janvier, 53940 Le Genest-Saint-Isle, France) are placed in groups of 4-5 in macrolon cages (41×25×18 cm or 44×28×19 cm) on wood litter (Litalabo—SPPS, 95100 Argenteuil, France), with free access to food and water until tested, and maintained under artificial lighting (12 hours) between 7:00 and 19:00 in a controlled ambient temperature of about 21° C., and relative humidity between 30-80%. Animals are acclimatized to laboratory conditions for least 3 days. Animals surviving the experiments are sacrificed at the end of the experiments by exposure to a mixture of $O_2/CO_2$ (20%/80%) followed by $CO_2$.

Dimebon, or an analog or derivative thereof, either alone or in combination with one or more other compounds as described herein, is evaluated at 3 doses (e.g. 1, 3, and 10 mg/kg), administered i.p. once daily for seven days, with a administration volume of 5 mL/kg. The last administration (7th) is injected 30 minutes prior to kainic acid administration, and compared with a vehicle control group. The test article (single compound or combination) is prepared in 0.2% HPMC in physiological saline as follows: The test article is tested for solubility by cold stirring of the highest intended dose for 10 minutes in physiological saline. If soluble, physiological saline serves as vehicle, and doses are prepared W/V (stock) and then V/V (serial dilutions). Preparations may be made freshly for each day of administration and precautions may be taken to preserve the homogeneity of suspensions (if applicable) during the period of administration.

Diazepam (4 mg/kg i.p.) is administered in 0.2% HPMC in physiological saline 30 minutes prior to KA, and is used as reference substance (positive control). Kainic acid (12 mg/kg i.p.) dissolved in physiological saline is administered 30 minutes following the 7th administration of test article, diazepam, or vehicle control. Additional details are described in Ben-Ari et al, Neuroscience, 6, 1361-1391, 1981 for detecting anticonvulsant activity related to a glutamatergic mechanism.

Animals are injected with kainic acid (12 mg/kg i.p.). The occurrences of the following symptoms are noted over a 120 minute period after kainic acid injection: wet-shakes, rearings, and rearings with forelimb clonus. The primary outcome measure will be a binary measure of whether each rat displays forelimb clonus following KA administration (0: no; 1: yes). In addition, the latencies to the first appearance of the symptoms are measured and the number of forelimb clonus are counted. The number of forelimb clonus episodes per time interval starting from the first occurrence of forelimb clonus will be considered regarding the severity scale. 10 animals are studied per group. The test is performed blind. Quantitative data is analyzed by comparing treated groups with vehicle control using unpaired Student's t tests. Quantal data is analyzed by comparing treated groups with vehicle control using Fisher's Exact Probability tests. The results for dimebon are shown in the following table.

| Compound[a] | Wet-shakes | | Rearings | | Rearings with Forelimb Clonus | | Forelimb Clonus |
| | Presence[b] | Latency[c] | Presence | Latency | Presence | Latency | No.[d] |
|---|---|---|---|---|---|---|---|
| Vehicle | 10 | 2456 (197)[e] | 9 | 3959 (518) | 10 | 5038 (310) | 2.8 (0.5)[f] |
| Dimebon | | | | | | | |
| 1 | 8 NS −20%[g] | 3615 NS (613) t = 1.8 p = 0.10 +47%[h] | 6 NS −33% | 4896 NS (653) t = 1.1 p = 0.28 +24% | 7 NS −30% | 6009 * (321) t = 2.2 p = 0.043 +19% | 1.9 NS (0.5) t = 1.2 p = 0.25 −32% |
| 3 | 10 NS 0% | 2666 NS (176) t = 0.79 p = 0.44 +9% | 9 NS 0% | 4134 NS (391) t = 0.27 p = 0.79 +4% | 9 NS −10% | 5366 NS (416) t = 0.63 p = 0.54 +7% | 2.5 NS (0.6) t = 0.37 p = 0.71 −11% |
| 10 | 10 NS 0% | 2865 NS (235) t = 1.3 p = 0.20 +17% | 8 NS −11% | 4526 NS (522) t = 0.77 p = 0.45 +14% | 9 NS −10% | 5410 NS (253) t = 0.93 p = 0.37 +7% | 2.3 NS (0.4) t = 0.77 p = 0.45 −18% |
| Diazepam | | | | | | | |
| 4 | 9 NS −10% | 3753 * (405) t = 2.9 p = 0.013 +53% | 9 NS 0% | 4282 NS (427) t = 0.48 p = 0.64 +8% | 4 * −60% | 6841 *** (200) t = 4.9 p = 0.0002 +36% | 0.6 ** (0.3) t = 3.8 p = 0.0020 −79% |

[a]Except for vehicle control, dose amount in mg/kg administered i.p. once daily on each of days 1 to 6, then 30 min before kainic acid administration on day 7;
[b]Presence observed out of 10 test animals; significance determined with Fisher's Exact test,
NS = not significant,
* = p < 0.05;
[c]average time in seconds calculated from all animals in group; significance determined with Student's t test (unequal variances),
NS = not significant,
* = p < 0.05,
** = p < 0.01,
*** = p < 0.001;
[d]average number observed calculated from all animals in group; ±s.e.m. in parenthesis; significance determined with Student's t test (unequal variances),
NS = not significant,
* = p < 0.05,
** = p < 0.01,
*** = p, 0.001;
[e]±s.e.m.;
[f]±s.e.m.;
[g]% change from vehicle;
[h]% change from vehicle.

Example

Acute Anticonvulsant Activity Using the Kainic Acid Seizure Test in Rat. Dimebon, or an analog or derivative thereof, including the compounds described herein, is shown to be efficacious in the rat kainic acid anticonvulsant activity model. The prior Example is followed with the exception that the test article, dimebon, or an analog or derivative thereof, either alone or in combination with one or more other compounds as described herein, is evaluated at a single dose of 100 mg/kg, administered i.p., with a administration volume of 5 mL/kg, 60 minutes prior to kainic acid administration, and compared with a vehicle control group. The 100 mg/kg formulation is prepared in 0.2% HPMC in physiological saline. The results for dimebon are shown in the following table.

| Compound[a] | Wet-shakes Presence[b] | Wet-shakes Latency[c] | Rearings Presence | Rearings Latency | Rearings with Forelimb Clonus Presence | Rearings with Forelimb Clonus Latency | Forelimb Clonus No.[d] |
|---|---|---|---|---|---|---|---|
| | | | Dimebon | | | | |
| 100 | 5 NS −50%[e] | 4394 NS (836) $t = 2.3$ $p = 0.055$ +79%[f] | 2 * −78% | 6197 * (707) $t = 2.6$ $p = 0.023$ +57% | 6 NS −40% | 4546 NS (866) $t = 0.54$ $p = 0.60$ −10% | 1.3 NS (0.5) $t = 2.1$ $p = 0.057$ −54% |

[a] Except for vehicle control, dose amount in mg/kg administered i.p. once daily on each of days 1 to 6, then 30 min before kainic acid administration on day 7;
[b] Presence observed out of 10 test animals; significance determined with Fisher's Exact test,
NS = not significant,
* = $p < 0.05$;
[c] average time in seconds calculated from all animals in group; significance determined with Student's t test (unequal variances),
NS = not significant,
* = $p < 0.05$,
** = $p < 0.01$,
*** = $p < 0.001$;
[d] average number observed calculated from all animals in group; ±s.e.m. in parenthesis; significance determined with Student's t test (unequal variances),
NS = not significant,
* = $p < 0.05$,
** = $p < 0.01$,
*** = p, 0.001;
[e] % change from vehicle;
[f] % change from vehicle.

Example

One or more dimebolins, such as Dimebon (20 mg total) is administered three times daily to a patient suffering from or in need of relief from epilepsy, or an epileptic condition. Illustratively, the dimebon in the form of tablets (comprising 10 mg or 20 mg of dimebon, 30 mg of lactose, and 5 mg of magnesium stearate) for oral administration. The duration of treatment in this and other examples described herein is determined according to the progression of epilepsy in each individual patient and dose adjustments are made accordingly. Treatment efficacy in this and other examples described herein is monitored by self-reporting and the results of treatment are evaluated statistically using Student's t-test and/or Fisher's "Fi" criterion.

Example

One or more dimebolins, such as Dimebon (25 mg total) is administered three times daily to a patient suffering from or in need of relief from epilepsy, or an epileptic condition. Illustratively, the dimebon in the form of tablets (comprising 12.5 mg or 25 mg of dimebon, 30 mg of lactose, and 5 mg of magnesium stearate) for oral administration. The duration of treatment in this and other examples described herein is determined according to the progression of epilepsy in each individual patient and dose adjustments are made accordingly. Treatment efficacy in this and other examples described herein is monitored by self-reporting and the results of treatment are evaluated statistically using Student's t-test and/or Fisher's "Fi" criterion.

Example

One or more dimebolins, such as Dimebon (30 mg total) is administered three times daily to a patient suffering from or in need of relief from epilepsy, or an epileptic condition. Illustratively, the dimebon in the form of tablets (comprising 15 mg or 30 mg of dimebon, 45 mg of lactose, and 7.5 mg of magnesium stearate) for oral administration. The duration of treatment in this and other examples described herein is determined according to the progression of epilepsy in each individual patient and dose adjustments are made accordingly. Treatment efficacy in this and other examples described herein is monitored by self-reporting and the results of treatment are evaluated statistically using Student's t-test and/or Fisher's "Fi" criterion.

Example

One or more dimebolins, such as Dimebon (30 mg total) is administered twice daily to a patient suffering from or in need of relief from epilepsy, or an epileptic condition. Illustratively, the dimebon in the form of tablets (comprising 15 mg or 30 mg of dimebon, 45 mg of lactose, and 7.5 mg of magnesium stearate) for oral administration. The duration of treatment in this and other examples described herein is determined according to the progression of epilepsy in each individual patient and dose adjustments are made accordingly. Treatment efficacy in this and other examples described herein is monitored by self-reporting and the results of treatment are evaluated statistically using Student's t-test and/or Fisher's "Fi" criterion.

Example

One or more dimebolins, such as Dimebon (40 mg total) is administered twice daily to a patient suffering from or in need of relief from epilepsy, or an epileptic condition. Illustratively, the dimebon in the form of tablets (comprising 20 mg or 40 mg of dimebon, 60 mg of lactose, and 10 mg of magnesium stearate) for oral administration. The duration of treatment in this and other examples described herein is determined according to the progression of epilepsy in each individual patient and dose adjustments are made accordingly. Treatment efficacy in this and other examples described herein is monitored by self-reporting and the results of treatment are evaluated statistically using Student's t-test and/or Fisher's "Fi" criterion.

Example

One or more dimebolins, such as Dimebon (50 mg total) is administered twice daily to a patient suffering from or in need of relief from epilepsy, or an epileptic condition. Illustratively, the dimebon in the form of tablets (comprising 25 mg or 50 mg of dimebon, 60 mg of lactose, and 10 mg of magnesium stearate) for oral administration. The duration of treatment in this and other examples described herein is determined according to the progression of epilepsy in each individual patient and dose adjustments are made accordingly. Treatment efficacy in this and other examples described herein is monitored by self-reporting and the results of treatment are evaluated statistically using Student's t-test and/or Fisher's "Fi" criterion.

Example

Dimebon is administered as described herein, such as oral administration of 20 mg, 25 mg, or 30 mg, three times daily, and co-administered with oral simvastatin (20 mg tablet, Merck & Co Inc) two times daily.

Example

Dimebon is administered as described herein, such as oral administration of 20 mg, 25 mg, or 30 mg, three times daily, and co-administered with oral sodium valproate tables (500 mg, Sanofi-Aventis) three times daily.

Example

Dimebon is administered as described herein, such as oral administration of 20 mg, 25 mg, or 30 mg, three times daily, to a patient diagnosed with Juvenile Myoclonic Epilepsy, and co-administered with oral simvastatin (20 mg tablet, Merck & Co Inc) two times daily, and co-administered with oral sodium valproate (500 mg tablet, Sanofi-Aventis) three times daily.

Example

Dimebon is administered as described herein, such as oral administration of 20 mg, 25 mg, or 30 mg, three times daily, to a patient diagnosed with juvenile typical absence epilepsy, and co-administered with 20 mg oral memantine (10 mg, twice daily). In one variation, treatment is started with 5 mg (once daily) of dimebon (half a tablet in the morning) during the 1st week, 10 mg per day (half a tablet twice a day) in the 2nd week, 15 mg per day (one tablet in the morning and half a tablet in the afternoon or evening) in the 3rd week, and then the recommended maintenance dose of 20 mg per day (one tablet twice a day) in the 4th week and beyond. In another variation, treatment is started with 5 mg (once daily, half a tablet in the morning) with memantine during the 1st week, 10 mg per day (half a tablet twice a day) in the 2nd week, 15 mg per day (one tablet in the morning and half a tablet in the afternoon or evening) in the 3rd week, and then the recommended maintenance dose of 20 mg per day (one tablet twice a day) in the 4th week and beyond.

Example

Dimebon is administered as described herein, such as oral administration of 20 mg, 25 mg, or 30 mg, three times daily, to a patient diagnosed with juvenile absence epilepsy, and co-administered with oral ethosuximide (250 mg tablet, Pfizer) three times daily.

Example

Dimebon is administered as described herein, such as oral administration of 20 mg, 25 mg, or 30 mg, three times daily, to a patient diagnosed with juvenile absence epilepsy, and co-administered with oral sodium valproate tables (500 mg, Sanofi-Aventis) two times daily.

Example

Dimebon is administered as described herein, such as oral administration of 20 mg, 25 mg, or 30 mg, three times daily, to a patient diagnosed with complex partial seizures, and co-administered with oral oxcarbamazepine (600 mg tablet) three times daily.

Example

Dimebon is administered as described herein, such as oral administration of 2×25, 2×50, or 2×100 mg three times daily, to a patient diagnosed with juvenile typical absence epilepsy, and co-administered with 20 mg oral memantine (10 mg, twice daily). In one variation, treatment is started with 25 mg (once daily) of dimebon during the 1st week, 2×25 mg per day in the 2nd week, 3×25 mg per day in the 3rd week, and then the recommended maintenance dose of 2×50 mg per day in the 4th week and beyond. In another variation, treatment is started with 25 mg (once daily) with memantine during the 1st week, 2×25 mg per day in the 2nd week, 3×25 mg per day in the 3rd week, and then the recommended maintenance dose of 2×50 mg per day in the 4th week and beyond.

Example

Dimebon is administered as described herein, such as oral administration of 100 mg, three times daily, to a patient diagnosed with juvenile absence epilepsy, and co-administered with oral ethosuximide (250 mg tablet, Pfizer) three times daily.

Example

Dimebon is administered as described herein, such as oral administration of 100 mg, three times daily, to a patient diagnosed with juvenile absence epilepsy, and co-administered with oral sodium valproate tables (500 mg, Sanofi-Aventis) two times daily.

Example

Dimebon is administered as described herein, such as oral administration of 100 mg, three times daily, to a patient diagnosed with complex partial seizures, and co-administered with oral oxcarbamazepine (600 mg tablet) three times daily.

What is claimed is:

1. A method for reducing seizures or delaying seizure onset in epilepsy characterized by recurrent unprovoked seizures in a patient, the method comprising the step of administering to the patient a therapeutically effective amount of one or more dimebolins, or pharmaceutically acceptable salts thereof, or combinations thereof as the only active pharmaceutical ingredients.

2. The method of claim 1 wherein the one or more dimebolins are compounds of formula (I)

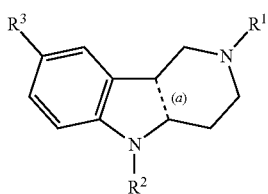

(I)

wherein $R^1$ is alkyl or arylalkyl; $R^2$ is hydrogen, benzyl, or 6-methylpyridinyl-3-ethyl; $R^3$ is hydrogen, alkyl, or halo and bond (a) is a single bond or a double bond.

3. The method of claim 1 wherein the one or more dimebolins are compounds of formula (II)

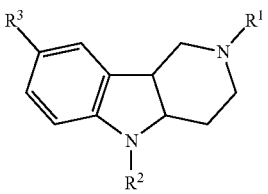

(II)

or a pharmaceutically acceptable salt thereof, wherein $R^1$ is alkyl or arylalkyl; $R^2$ is hydrogen, benzyl, or 6-methylpyridinyl-3-ethyl; $R^3$ is hydrogen, alkyl, or halo.

4. The method of claim 1 wherein the one or more dimebolins are compounds of formula (III)

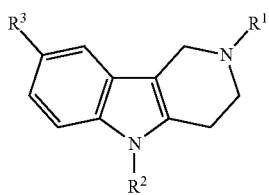

(III)

or a pharmaceutically acceptable salt thereof, wherein $R^1$ is alkyl or arylalkyl; $R^2$ is hydrogen, benzyl, or 6-methylpyridinyl-3-ethyl; $R^3$ is hydrogen, alkyl, or halo.

5. The method of claim 1 wherein at least one dimebolin is 2-methyl-5-[2-(6-methyl-3-pyridyl)ethyl]-2,3,4,5-tetrahydro-1H-pyrido[4,3-b]indole or a pharmaceutically acceptable salt thereof.

6. The method of claim 1 wherein the disease epilepsy is a generalized epilepsy.

7. The method of claim 6 wherein the generalized epilepsy is tonic-clonic epilepsy.

8. The method of claim 6 wherein the generalized epilepsy is clonic epilepsy.

9. The method of claim 6 wherein the generalized epilepsy is absence epilepsy.

10. The method of claim 6 wherein the generalized epilepsy is tonic epilepsy.

11. The method of claim 6 wherein the generalized epilepsy is myoclonic epilepsy.

12. The method of claim 6 wherein the generalized epilepsy is atonic epilepsy.

13. The method of claim 6 wherein the generalized epilepsy is reflex epilepsy.

14. The method of claim 1 wherein the epilepsy is a focal epilepsy.

15. The method of claim 14 wherein the focal epilepsy is focal sensory epilepsy.

16. The method of claim 14 wherein the focal epilepsy is focal motor epilepsy.

17. The method of claim 14 wherein the focal epilepsy is gelastic epilepsy.

18. The method of claim 1 wherein the dimebolin is dimebon or a salt thereof.

19. The method of claim 6 wherein the dimebolin is dimebon or a salt thereof.

20. The method of claim 14 wherein the dimebolin is dimebon or a salt thereof.

* * * * *

UNITED STATES PATENT AND TRADEMARK OFFICE
CERTIFICATE OF CORRECTION

Page 1 of 1

PATENT NO. : 11,389,435 B2
APPLICATION NO. : 16/784362
DATED : July 19, 2022
INVENTOR(S) : Spyros Deftereos et al.

It is certified that error appears in the above-identified patent and that said Letters Patent is hereby corrected as shown below:

In the Claims

Column 30, In Claim 6, Line 19, "wherein the disease epilepsy," should read - wherein the epilepsy -.

Signed and Sealed this
Thirtieth Day of August, 2022

Katherine Kelly Vidal
*Director of the United States Patent and Trademark Office*